United States Patent
Bergs

[11] Patent Number: 6,148,676
[45] Date of Patent: Nov. 21, 2000

[54] TENSILE TESTING MACHINE

[75] Inventor: Sune Bergs, Falun, Sweden

[73] Assignee: Bergs Engineering AB, Faulun, Sweden

[21] Appl. No.: 09/171,021
[22] PCT Filed: Apr. 9, 1997
[86] PCT No.: PCT/SE97/00588
 § 371 Date: Oct. 9, 1998
 § 102(e) Date: Oct. 9, 1998
[87] PCT Pub. No.: WO97/39331
 PCT Pub. Date: Oct. 23, 1997

[30] Foreign Application Priority Data

Apr. 12, 1996 [SE] Sweden .................................. 9601402

[51] Int. Cl.$^7$ ...................................................... G01N 3/08
[52] U.S. Cl. ................................................ 73/833; 73/800
[58] Field of Search ............................. 73/800, 826, 833, 73/831, 840

[56] References Cited

U.S. PATENT DOCUMENTS

| | | |
|---|---|---|
| 4,019,378 | 4/1977 | Keller et al. . |
| 4,112,746 | 9/1978 | Itoh et al. ................................. 73/789 |
| 4,777,358 | 10/1988 | Nelson .................................... 250/225 |
| 4,841,779 | 6/1989 | Mitsuhashi et al. ...................... 73/826 |
| 4,962,669 | 10/1990 | Gernhart et al. .......................... 73/800 |
| 5,193,398 | 3/1993 | Harder et al. . |
| 5,568,259 | 10/1996 | Kamegawa .............................. 356/373 |

FOREIGN PATENT DOCUMENTS

| | | |
|---|---|---|
| 3537248 | 6/1988 | Germany . |
| 3813340 | 11/1988 | Germany . |

*Primary Examiner*—Max Noori
*Attorney, Agent, or Firm*—Young & Thompson

[57] ABSTRACT

Tensile testing device, which measures the strain for a tensile testing specimen (24) by means of the relative displacement of the fastening means (2, 14), as a result of that the attachment of the tensile testing specimen (24) is performed in such a manner which is independent of the applied tensile testing force. Furthermore, the device provides a contact-free dimension measurement (26, 27) of the tensile testing specimen (24) simultaneous to the tensile testing procedure. The device enables at the same time a compensation of measured values for machine strain and friction forces, and the pulling speed in the tensile testing procedure is controllable, depending in the appearance of the tensile test curve. Moreover, the maximum tensile stress, various standardised strain measures and the fracture area may be calculated.

11 Claims, 5 Drawing Sheets

TENSILE TESTING MACHINE

TECHNICAL FIELD

The present invention generally relates to a device and a method for tensile testing of materials, in particular metallic materials.

BACKGROUND OF THE INVENTION

Tensile testing of materials is nowadays one of the most common ways to measure and check material dependent properties. Such tests can give almost any material data a designer need to know.

For tensile testing a tensile testing specimen is normally mounted between two attachment devices. One of the devices is normally arranged at a frame, while the other is arranged at a movable pulling yoke. The pulling yoke is displaced so as to elongate the tensile testing specimen, which finally breaks. The most interesting quantities to be measured is the strain of the tensile testing specimen and the tensile force of the pulling yoke. The relation between strain and tensile force may be recorded as the pulling continues. Other interesting quantities, often required to be determined is the fracture area, the maximum tensile force, and the strain at fracture.

In tensile testing devices according to the state of the art the tensile testing specimens are attached by wedging jaw means. These operate so as to fasten the tensile testing specimen harder as the tensile force increases. Such arrangements often give a simple and safe attachment without need for external fastening mechanisms, but have the inherent disadvantage that the tensile testing specimen moves slightly with respect to the fastening devices during the tensile testing itself, and in particular at its beginning. This disadvantage results in that the displacement of the fastening devices is unable to give any true measurement of the strain of the tensile testing specimen, why other means generally are used for strain measuring.

Strain sensors, which are in contact with the tensile testing specimen, are a common type of measuring devices. They may consist of pure mechanical arrangements, electromagnetic devices or strain gauges. Common to all these types of strain sensors is that they have to be attached with accuracy at the tensile testing specimen, which makes them inconvenient for automatic testing constructions. Furthermore, there is a large risk that the sensors are broken or damaged when the tensile testing specimen reaches fracture.

Contact-free strain sensors are more suited for automatic testing, since the above mentioned disadvantages are avoided. The most common methods are to, on the tensile testing specimen, scribe or in any other manner apply a mark, whose displacement then may be followed by different recording instruments. In the patent publication U.S. Pat. No. 5,193,398, a device for strain measuring is disclosed, which uses a recording of a lattice by means of a CCD camera. Common for the contact-free strain sensors according to the state of the art is that they all require some kind of marking of the tensile testing specimen, which on one hand involves an extra operation and on the other hand may run the risk of changing the properties of the tensile testing specimen somewhat.

Tensile testing according to the state of the art operates almost exclusively with a constant pulling speed, which is achieved by adjusting the tensile force. However, in a tensile test curve, the most important information is to find in the areas where the change of the force is large, which results in that the accuracy of measurements of certain measures will suffer, since these regions are passed rapidly. On the contrary, there are many parts in a tensile test curve, which are fairly uninteresting, but where the force change is small, why these areas are passed slowly. Accordingly, the time of the tensile testing is used very inefficiently.

One area of particular interest is the area immediately before fracture. For tensile testing according to the state of the art, this part is passed rapidly and only a little information is available by the tensile test curve. One interesting measure is the area of the fracture, and according to the state of the art, this area is measured by hand after the completion of the fracture. It is obvious that a manual step of operation of this kind introduces large uncertainties in the measuring, particularly as the surface of the fracture is irregular. The procedure is also comparatively time consuming. For many tensile testing specimens, the surface of fracture is not simply definable, why different models for making the measurement will influence the result.

The quantities which are measured during tensile testing are according to the state of the art related to the original area of the tensile testing specimen. The measure of the area varies during the tensile testing and knowledge about this variation is interesting in many aspects. No tensile testing equipment according to the state of the art can provide such an information.

By tradition, the majority of the tensile testing equipments are arranged in a vertical configuration, often leading to unergonomic working positions at sample mounting, adjustment and measuring. Furthermore, a vertical configuration is difficult to combine with an automatic feeding of tensile testing specimens.

DISCLOSURE OF THE INVENTION

The object of the present invention is to provide a device and a method for tensile testing, which do not present the above mentioned disadvantages. The device and the method according to the invention makes it possible to, in an accurate and automatic manner, carry through tensile testing measurements, where the strain measuring is accomplished contact-free and without requesting that the tensile testing specimen has to be marked before the measurement. In a preferred embodiment, the pulling speed is adjusted in order to obtain an as time efficient measuring as possible. The device and the method of the preferred embodiment makes it possible to achieve a measure of the area of fracture of the tensile testing specimen without need for using manual measuring. Furthermore, it is also possible to achieve a continuos measuring of the diameter of the tensile testing specimen during the entire tensile testing course. Moreover, the entire device is adjusted to provide an maximum ergonomic working position for the operator.

BRIEF DESCRIPTION OF THE FIGURES

Other features are evident from the following detailed descriptions in connection with the enclosed drawings, in which.

DETAILED DESCRIPTION OF AN EMBODIMENT

Figure 1:
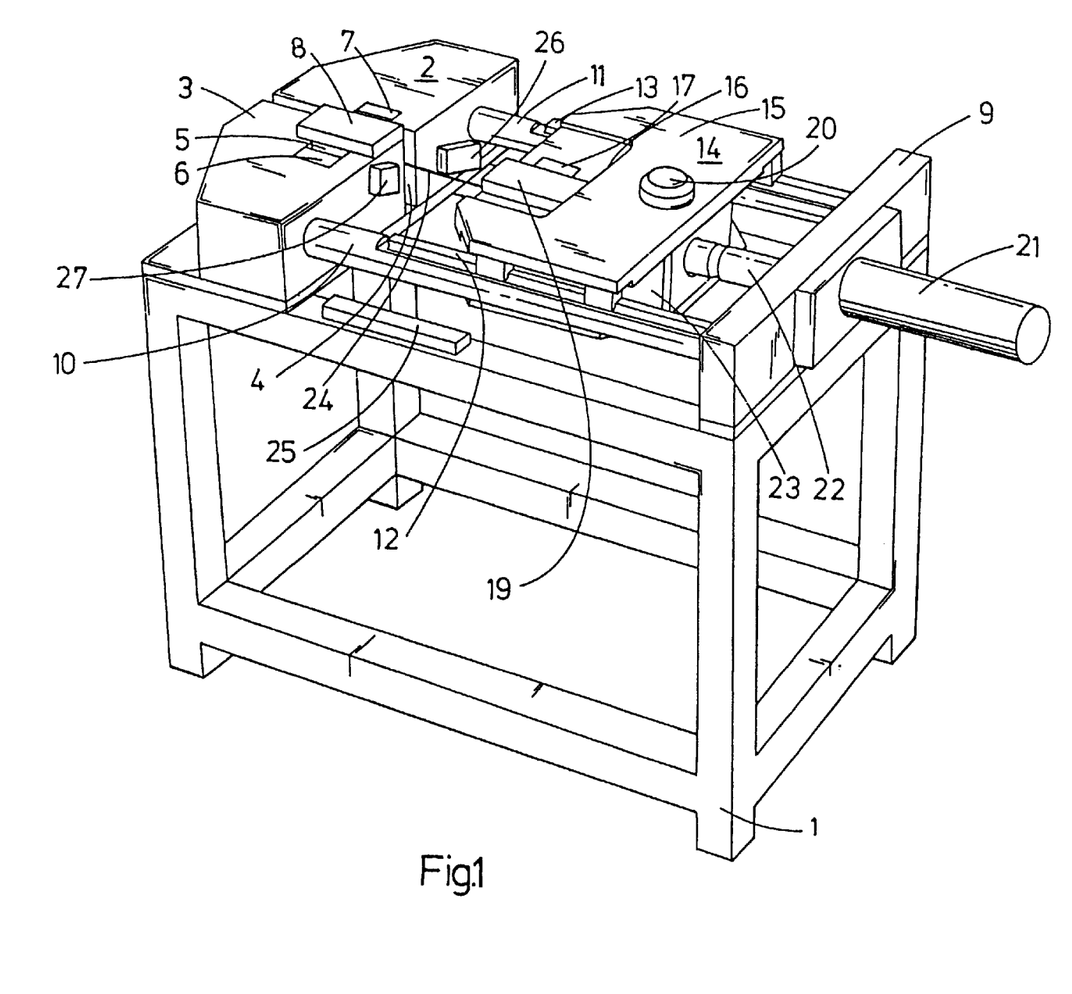
FIG. 1 is a sketch of an embodiment of the present invention.

FIG. 1 illustrates a preferred embodiment of the invention. The tensile testing device is fixed within a frame 1. A first fastening means 2 comprises in this embodiment a first end block 3, which is fixedly fastened at one end of the frame 1. The first end block 3 has a recessed volume 5 in that end which is directed towards the centre of the frame. In this volume, two inserts 6, 7 for clamping jaws, are arranged, of which one is displaceable 6 by means of hydraulics and one is fixed 7. Below a plate 8, a clamping means is disposed, which will be described in detail below and to which the inserts 6 and 7 belong. The clamping means together with the recessed volume 5 of the end block 3 forms a relatively narrow slit 4 directed towards the centre of the device.

At the other end of the frame 1 is a second end block 9 fixedly fastened. Between the first and the second end block 3 and 9, respectively, two parallel strong linear shafts 10, 11 are disposed. On each of the linear shafts a portion of the upper section is recessed so as to form a planar surface, and on these recessed surfaces are one respective linear rail 12, 13 fixedly disposed.

A second fastening means 14, comprises in this embodiment a displaceable clamping jaw housing 15, which is slideably supported of the linear shafts 12, 13 by a number of linear carriages. By the linear carriages, the linear rails 12, 13 conduct the clamping jaw housing 15 in such a way that it only is displaceable rectilinearly along the linear shafts 12, 13 and is not rotateable or displaceable in any other direction. The clamping jaw housing 15 is provided with a recess 16 in that side which is directed towards the first end block 3. In this recess are, like as in the first end block, two inserts 17, 18 for clamping jaws disposed, one fixed 17 and one displaceable 18. Below a plate 19 is a clamping means disposed, which is formed in an analogue way with that in the first end block 3.

The clamping jaw housing is in that side which is directed towards the second end block 9 formed by two parallel plates, separated by a cavity 23. Through the clamping jaw housing 15, near the side which is directed towards the other end block 9, an opening is formed in each plate. A load cell 20 is introduced through these openings. The load cell 20 is arranged with flange bushings with its end portions against the plates of the clamping jaw housing 15 to be fixed in relation to these. A hydraulic cylinder is fixedly attached at the outside of the second end block 9 and a rod piston 22 of the hydraulic cylinder 21 extends through an opening in the second end block 9, in the direction towards the clamping jaw housing 15. The cavity 23 of the clamping jaw housing 15 is disposed so as to extend around the area of the load cell 20. The end of the rod piston 22 of the hydraulic cylinder 20 protrudes into this cavity 23 and is connected to the centre portion of the load cell 20.

Figure 2:
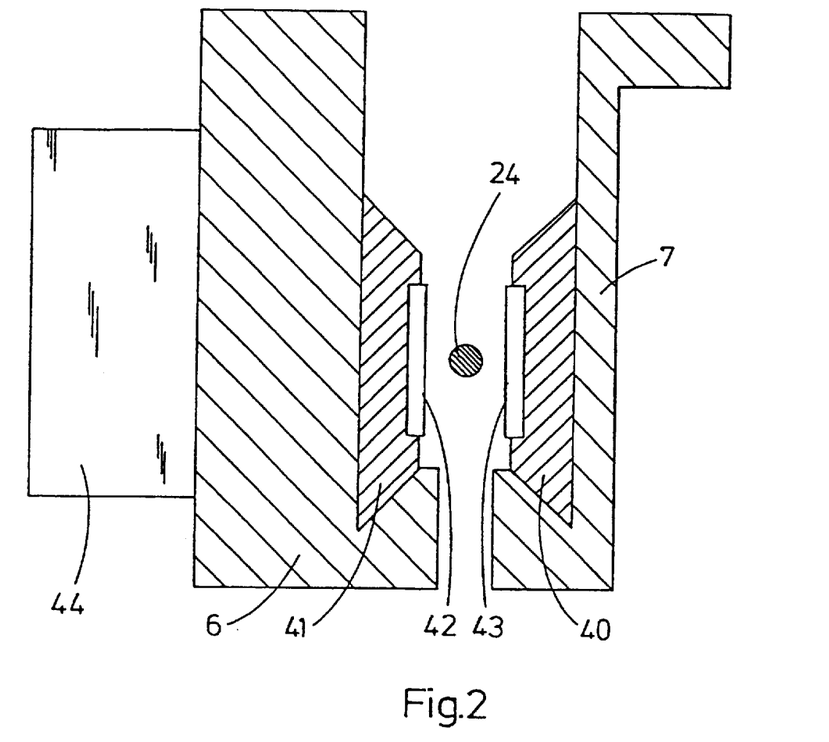
FIG. 2 is a sketch of a fastening means according to the embodiment shown in FIG. 1.

In FIG. 2, clamping means is shown, comprising a first clamping jaw 40 and a second clamping jaw 41, which are mounted in the fixed insert 7 and the movable insert 6, respectively, in the recessed volume 5 in the first end block 3. The clamping jaws 40, 41 consist of hardened steel and a clamping surface 42, 43 on each jaw is grinded with grooves in order to clutch the tensile testing specimen 24. The clamping jaws 40, 41 may alternatively have insertions of grooved hard metal, which then constitutes the clamping surfaces 42, 43. The clamping jaws are blocked in the pulling direction by at the inserts fixedly attached supports (not shown) and in the opposite direction by springs. This arrangement holds the jaws exactly in position during the tensile testing. It is possible to change the clamping jaws when they are not loaded without need for any tools by pushing the clamping jaws upwards. An hydraulic unit 44 is disposed at the moveable insert 6 to displace the second clamping jaw 41 against the first clamping jaw 40 and thereby clamp the tensile testing specimen 24 between the clamping jaws 40, 41.

Corresponding arrangement of inserts, clamping jaws and hydraulic unit is present in the clamping jaw housing 15 for clamping of the other end of the tensile testing specimen.

An hydraulic system, which is not shown in FIG. 1, provides the hydraulic cylinder 21 and the clamping means with hydraulic pressure to drive the rod piston 22 and squeeze the clamping jaws 40, 41 together, respectively. The control of the hydraulic pressures is managed by a control device which in its turn is connected to a logical unit.

The load cell 20 comprises a number of strain sensors, which measure the bending of the load cell 20. The bending of the load cell 20 may by someone skilled in the art simply be related to the applied tensile force on the clamping jaw housing 15, why the bending represents a measure of the applied force. A linear position sensor 25 is disposed at the frame 1 and detects the displacement of the clamping jaw housing 15.

Figure 3:
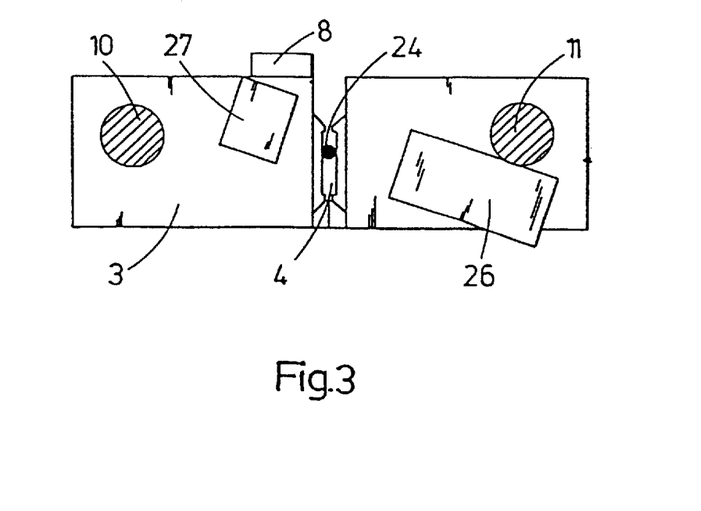
FIG. 3 is a sketch of the mounting of the contact-free dimension meter according to the embodiment shown in FIG. 1.

A contact-free dimension meter is disposed at the first end block 3, and comprises a laser beam source 26 and a reflector part 27. This part is better depicted in FIG. 3. The laser beam from the laser source 26 illuminates the tensile testing specimen 24 and the light that passes is reflected back in the reflector part 27 and detected by the laser beam source 26. The amount of light that is stopped by the tensile testing specimen 24 is proportional to the diameter of the tensile testing specimen 24 perpendicular to the direction of the light. The measured amount of light therefore represents a measure of the dimension of the tensile testing specimen 24. Such dimension meters are known per se and are commercially available, e.g. Mitutoyo Laser Scan Micrometer 544-432V, but have in the state of the art not been used for this purpose.

The tensile testing device is mounted horizontally, which simplifies for an operator to reach the sample position and to work with the mounting of the tensile testing specimen under ergonomical conditions.

Figure 4:
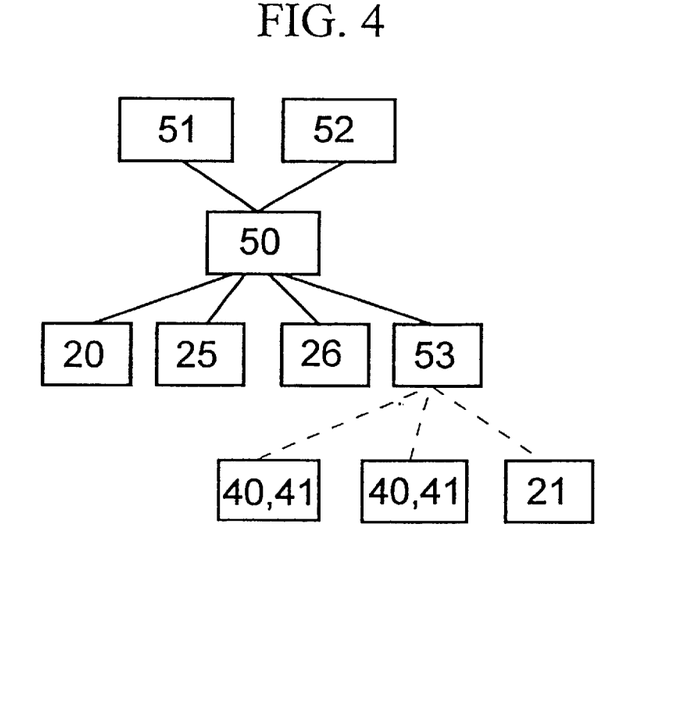
FIG. 4 is a block scheme, illustrating the connections of the included parts of the embodiment, shown in FIG. 1.

FIG. 4 shows schematically how the different parts of the control and measuring system of the device are connected. A logical unit 50 is the central point of the system. In this embodiment, the logical unit 50 comprises a microprocessor which is suitable for control and measurement result collection. Such microprocessors are well known by someone skilled in the art. To the logical unit is suitably an operating unit 51 and a presentation unit 52 connected. The operating unit may comprise a operating board and/or a key board so as to the operator may be able communicate with the different parts of the device. The presentation unit should better comprise a printer and/or a display. The function of such components are well known to someone skilled in the art and is therefore not described in more detail.

The logical unit 50 is further connected to the linear position sensor 25, the laser beam source 26 and the load cell 20 so that it from these units may read measurement results for the displacement of the clamping jaw housing 15, the diameter of the tensile testing specimen 24 and the tensile force of the hydraulic cylinder 21, respectively. Furthermore, the logical unit 50 is connected to a hydraulic system control means 53, which in turn controls the hydraulic pressure to the clamping jaws 40, 41 in the clamping jaw housing 15 and in the first end block 3, and to the hydraulic cylinder 21. The communication between the hydraulic system control means 53 and the logical unit 50 may besides control information from the logical unit 50 to the hydraulic system control means 53 also suitably mediate the condition information from the hydraulic system control means 53 to the logical unit 50.

A tensile testing specimen 24 is arranged with its ends between the clamping jaws 40, 41 in the first end block 3 and the clamping jaw housing 15, respectively. A hydraulic pressure is applied to the clamping jaws 40, 41, which grip the ends of the tensile testing specimen 24 with such a force that the points of attachment at the tensile testing specimen 24 can not move with respect to the clamping jaws 40. A hydraulic pressure is then applied in a controlled manner on the hydraulic cylinder 21, whereby the rod piston 22 applies a tensile force onto the clamping jaw housing 15 by the load cell 20. The function of the clamping jaws 40, 41 according to the invention is to form an attachment for the tensile testing specimen 24 which is not dependent on-the tensile force that is applied on the test sample. It is of particular importance that the clamping jaws 40, 41 grip the tensile testing specimen with such a force that the subsequently applied tensile force can not change the position of the tensile testing specimen 24 with respect to the jaws. By such a construction, the displacement of the clamping jaw housing 15 may be used as a measure of the strain of the tensile testing specimen, preferably after a correction for the strain of the machine. Accordingly, a strain measurement directly at the tensile testing specimen is avoided, which makes marking at the sample and attachment of strain gauges directly on the tensile testing specimen, respectively, dispensable.

Sometimes, it is necessary to adjust the tightenen force depending on which material is going to be tested and on the diameter of the tensile testing specimen. Accordingly, a preferred embodiment of the invention comprises a possibility to control the force, by which the tensile testing specimen is clamped in the tensile testing machine, based on information about the material and dimensions of the tensile testing specimen, which are fed into the system by the operating unit 51.

Figure 5:
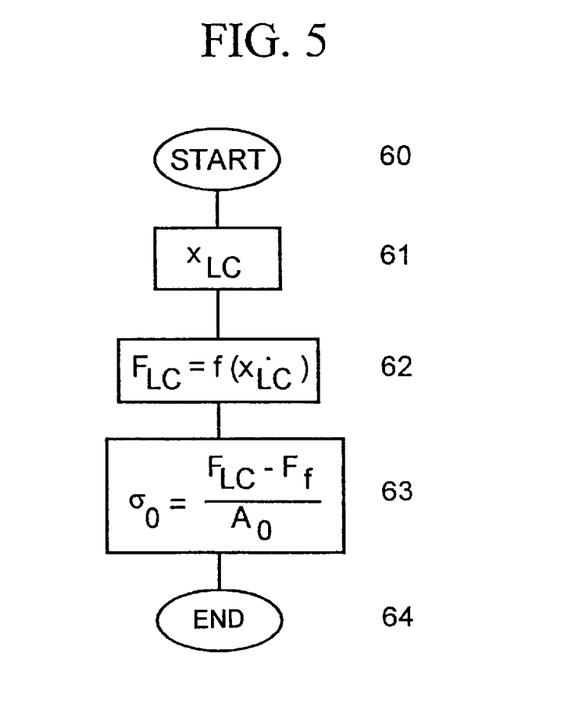
FIG. 5 is a block diagram, illustrating processing of test results according to the present invention.

During the tensile testing, the applied tensile stress is registered by the load cell 20 and the displacement of the clamping jaw housing 15 is registered by the linear position sensor 25. The measured tensile stress includes two terms, the actual tensile stress in the tensile testing specimen and the friction of the clamping jaw housing 15 against the linear shafts 10, 11. The latter term may easily be measured for each device. In a preferred embodiment, a processing of the measured value of the tensile stress is then performed, as shown in FIG. 5. The process begins at 60. At 61, the read value of the strain $x_{LC}$ of the load cell 20 is read into the logical unit 50. At 62, the strain measure is converted to a tensile force value $F_{LC}$ according to the specifications of the used load cell 20, which are defined by a function f(x). This tensile force value is subsequently in step 63 corrected for the measured friction forces $F_f$ against the linear shafts, which values are stored in the logical unit, and is converted to a nominal tensile stress value $\sigma_0$ by comparison with the original area $A_0$ of the tensile testing specimen. This original measure of the area $A_0$ is either supplied by the operator by the operating unit 51 or is measured by means of the dimension meter 26, 27. The process is then ended at 64.

Figure 6:
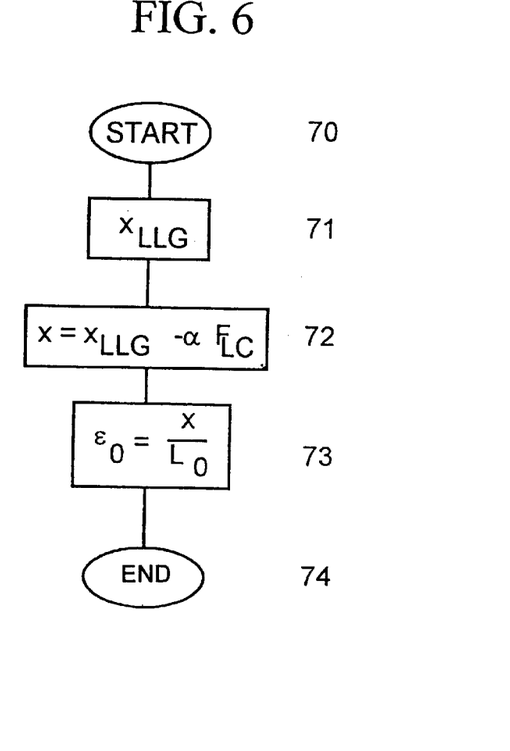
FIG. 6 is a block diagram, illustrating another processing of test results according to the present invention.

If the tensile testing specimen 24 have been secured between the clamping jaws 40, 41 in a prescribed manner, the fastening does not contribute to any displacement of the tensile testing specimen relative to the clamping jaw housing. The measured displacement of the clamping jaw housing 15 involves two terms, one which is dependent of the actual strain at the tensile testing specimen and one which is dependent in the strain of the machine. The strain of the machine may by a suitable construction of the involved parts be assumed to be proportional to the applied tensile force, and someone skilled in the art understands that this proportionality constant easily may be measured and stored in the logical unit. In a preferred embodiment, a processing of the measured value of the strain is performed, as shown in FIG. 6. The process begins at 70. At 71, the read value corresponding to the displacement $x_{LLG}$ is read into the logical unit 50. At 72, the displacement measure is corrected for the measured strain of the machine $\alpha \cdot F_{LC}$ to give a displacement value for the tensile testing specimen x. This displacement measure is at 73 converted to a nominal strain value $\epsilon_0$ by comparison with the original length $L_0$ of the tensile testing specimen. This original length $L_0$ may either by entered by the operator by the operating unit 51 or be measured by the linear position meter 25. The process is then ended at 74.

Figure 7:
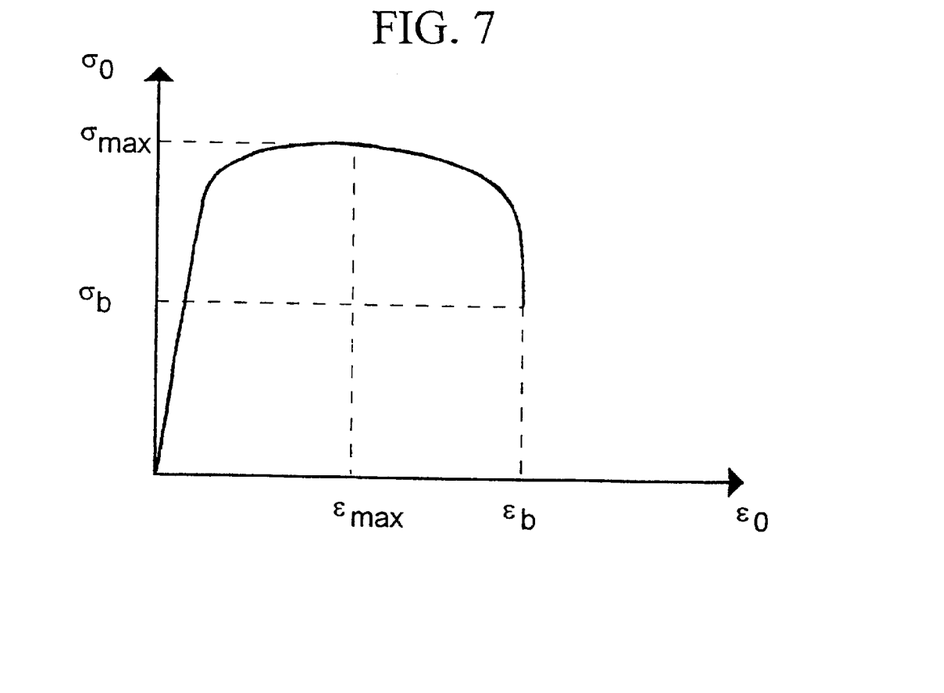
FIG. 7 is an example of a typical tensile test curve.

The true measures of the nominal tensile stress and strain of the tensile testing specimen obtained in this way are thus possible to register as the tensile testing proceeds. A diagram, illustrating a typical appearance of such a tensile test curve for steel, is shown in FIG. 7. At low tensile stress, the strain normally varies linearly with the tensile stress, i.e. the material is elastically strained. At larger strains, the tensile test curve levels away as soon as plastic deformation occurs. The tensile test curve goes through a point where a maximum tensile stress $\sigma_{max}$ is passed. Corresponding strain is denoted by $\epsilon_{max}$. In connection with this maximum, a waist normally starts to form on the tensile testing specimen. If the strain is further increased, a fracture point is reached with corresponding tensile stress value $\sigma_b$ and strain value $\epsilon_b$. By calculating a differential coefficient for a smoothed tensile test curve, it is possible to determine in which point the tensile test curve passes its maximum and thereby determine the values for $\sigma_{max}$ and $\epsilon_{max}$.

By the invention, a fast and accurate determination of the tensile test curve is achieved. Since the pulling speed is determined by the controlling of the hydraulic cylinder 21, whose control means 53 is connected to the logical unit 50, it is possible to control the pulling speed depending on the appearance of the tensile test curve. In the elastic interval, the tensile stress varies rapidly with the strain and by using a low pulling speed in this area, it is possible to obtain accurate measurements in this interval. In the plastic interval, no large changes occur, and the pulling speed may thus be increased without loosing any important information. Just before the fracture, the tensile stress normally decreases drastically, and for to be able to extrapolate a good value of the stress and strain at fracture, it is preferable if the pulling speed may be decreased to a minimum.

At fracture, the measurement is finished and the tensile test curve may be analysed in detail. A number of different strain measures for the tensile testing specimen usually are given and the most common is to state the strain for a certain length of the tensile testing specimen around the fracture area. Different standards state different lengths, of which the most common is: 5 times the diameter of the tensile testing specimen, 10 times the diameter of the tensile testing specimen, 100 mm, 5 inches and 10 inches. In conventional devices, such determinations are often performed by hand after the fracture has occurred. In a preferred embodiment of the present invention, these determinations are made by calculations based on the tensile test curve. By assuming that a volume calculation may be performed, i.e. that the strain up to the maximum tensile stress $\sigma_{max}$ is occurring homogeneously along the tensile testing specimen and thereafter only occurs in the area closest to the fracture point, the following relations may be used for the calculations of the strain measures:

$$\epsilon_D = \epsilon_{max} \cdot (1 - L_0/D) + \epsilon_b \cdot L_0/D \qquad (1)$$

where D is the suitable length for the strain measure. The result of these calculations may thus be presented immediately after the occurrence of the fracture together with the complete tensile test curve at the presentation unit, which enables the operator to quickly make a preliminary judgement of the test result.

The magnitude of the fracture area is of importance for evaluating the properties of the tensile testing specimen. The manual method used according to the state of the art involves large uncertainties, both concerning differences between different operators and in the definition of the circumference of the area. In the present invention, these disadvantages are avoided by using the tensile force at fracture as the starting point for calculation of the area of fracture. Thereby, an additional manual working step is avoided and also large uncertainties upon the determination.

When the tensile force drastically starts to decrease in the tensile test curve after the passage of the maximum point, the pulling speed is strongly reduced and the slowest possible pulling speed with maintained accuracy in the measurement of the strain is introduced. The tensile force decreases considerably until fracture occurs. The slower this last strain may be performed, the higher accuracy in the determination of the tensile force at fracture may be obtained. To effectuate such a controlling, the logical unit has to have access to the above calculated values for the tensile test curve and the calculation of the maximum tensile stress, which is possible by the method described above. Either the last measured value of the tensile force prior to fracture is used as a measure of the tensile force at fracture. An alternative way is to use a number of the last measuring point to fit a suitable curve and extrapolate a measure of the tensile force at fracture by assuming that the fracture occurred halfway to the next intended measuring point. Independent of the method of evaluation a well determined value, in comparison with other methods of evaluations, for the tensile force at fracture $F_b$ is obtained.

Furthermore, the fracture area $A_b$ may be determined by a comparison of the tensile force at fracture and the nominal tensile stress $\sigma_{max}$ at maximum. A still improved estimation is provided if the tensile force at fracture is compensated for the friction force $F_f$, which has been described above, and for the area contraction which sets in until the waist is developing at the tensile testing specimen. The latter term may be estimated from $\epsilon_{max}$. The calculation of the area of fracture may thus be obtained by the relation:

$$A_b = (F_b - F_f)/\sigma_{max} \cdot g(\epsilon_{max}) \qquad (2)$$

where g is a function which estimates the area reduction from the strain. The result from these calculations may thus immediately after the occurrence of the fracture be presented together with other calculated values and the complete tensile test curve at the presentation unit, which enables the operator to quickly make a preliminary judgement of the test result.

That the area of the tensile testing specimen decreases during the entire tensile testing process is a well known fact. The reduction in area is relatively small, except when and where the waist is formed. Normally, the nominal area of the tensile testing specimen is used as a standardisation to be able to state all tensile stresses. However, it is often interesting to be able to evaluate the true tensile stress, as, for instance, in the case with the area of fracture described above, whereby a measure of the true area is desirable. In a preferred embodiment of the present invention, a contact-free dimension meter is disposed in the tensile testing device. This laser micrometer 26, 27 provides information about the variation of the area during the tensile testing. The laser micrometer 26, 27 may e.g. provide the tensile testing device with a measure of the nominal area of the tensile testing specimen prior to the tensile testing, which is used by calculation of the nominal tensile stress, as described above. It may also contribute to improve the estimation of the fracture area, by providing information about the true diameter of the tensile testing specimen at maximum tensile stress. The correction factor f in the formula 2 above may then be replaced by another correction factor based on the measured area at maximum tensile stress $A_{max}$.

For many tensile tests, the area does not vary smoothly over the entire length of the tensile testing specimen, but strain sometimes only occurs in certain sections of the length of the tensile testing specimen. These sections varies during the procedure so that the average strain up to the maximum tensile stress is substantially the same over the entire length. By following the evolution of the local area reduction at a position at the tensile testing specimen, information about the homogeneity of the tensile testing specimen, crystal sizes etc. may be obtained. The invention enables the inclusion of such information directly together with the tensile test curve at the presentation unit, which in the same manner as above facilitates the evaluation of the test results.

Figure 8:
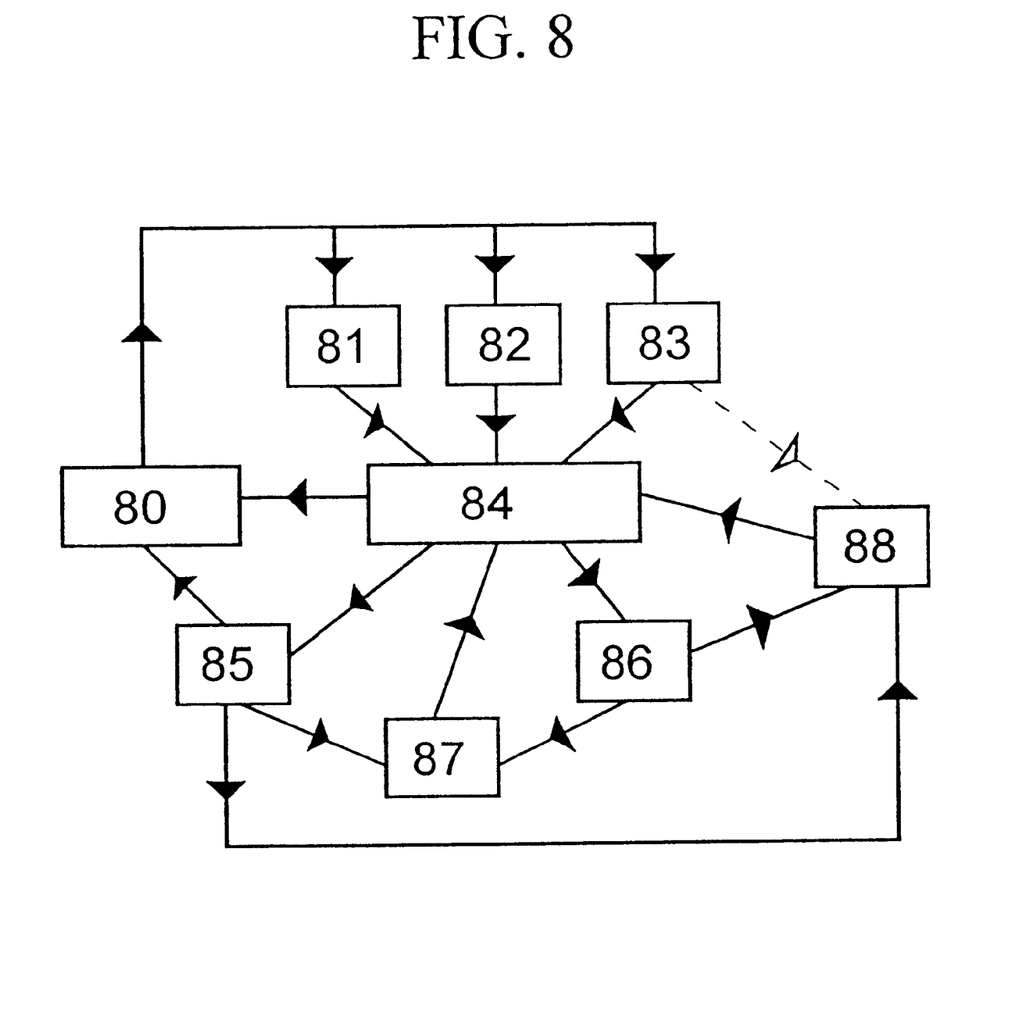
FIG. 8 schematically shows how the different components cooperate.

The above measurements, calculations and the controlling of the procedure of tensile testing are tied together with the result of the tensile testing procedure in a mutually depending manner. FIG. 8 schematically shows how the different components co-operate. The controlling of the pulling speed is denoted by 80. This pulling speed influences the measuring means of the device for measuring and conversion of tensile force 81, displacement 82 and the diameter of the tensile testing specimen 83. The tensile force is converted 81 to a measure of tensile stress according to the method shown in FIG. 5. The displacement is converted 82 to a measure of strain according to FIG. 6. These three quantities contributes to the presentation of the result of the tensile testing measurement 84, which in turn influences the subsequent control 80 of the pulling speed. From the result 84, the maximum tensile stress $\sigma_{max}$ and the strain at maximum tensile stress $\epsilon_{max}$ is determined, which is denoted by 85, and also after fracture, determination of tensile force and strain at fracture $F_b$ and $\epsilon_b$, respectively, which is denoted by 86. The controlling of the pulling speed 80 is also influenced by the determinations at maximum tensile stress 65. Furthermore, from both the determinations 85 and 86, a requested number of strain measures 87 are determined, which in turn are presented together with the result 84. From the determinations 85 and 86, the fracture area $A_b$ may further be determined 88. In this determination, the continuous measurement of the area of the tensile testing specimen 83 may be used, if requested. The fracture area is also presented together with the other results 84 to provide an easily comprehensible total picture of all essential results obtained from the tensile testing procedure.

The above description should be understood as an exemplifying embodiment of the present invention and no restrictions of the scope of the patent should be accepted from this description. Changes and modifications, which are obvious for someone skilled in the art should be included in the scope of the patent, as described in the claims. In that manner, it is thus possible to achieve a tensile force by using a controllable motor together with a screw arrangement to give the well controlled tensile force. The attachment of the tensile testing specimen in the clamping jaws may also be performed by motor driven screw arrangements. Furthermore, the implementing of the control system, the treatment of the measurement values and the calculations may be effectuated in different ways according to the state of the art. Likewise, it is also possible to have both attachment means for the tensile testing specimen movable and measure their relative distance change as a measure of the strain of the tensile testing specimen.

What is claimed is:

1. Method for material testing with a tensile testing device, comprising a first and a second fastening means for attachment of tensile testing specimen, pulling means for displacement of the fastening means relative to each other, means for strain measurement, means for measurement of tensile force, logical unit and presentation unit, said method comprising the steps of:

attaching a tensile testing specimen by clamping its ends in a first and second fastening means, respectively, whereby the clamping is performed by a force independent of the force of the pulling means;

displacement of the fastening means relative each other by applying a force by means of the pulling means;

measuring of the tensile force applied at the fastening means by the pulling means;

measuring of the strain of the tensile testing specimen, comprising measuring of the displacement of the fastening means relative to each other;

collecting measurement results from the means for strain measurements and the means for measuring the tensile force by the logical unit;

presenting measurement results at the presentation unit;

contact-free measuring of the diameter of the tensile testing specimen, whereby the contact-free measuring of the tensile testing specimen is performed simultaneously as the displacement of the fastening means;

presenting of the results of the contact-free measurement of the diameter of the tensile testing specimen together with the result of other results from the tensile testing at the presentation unit;

determining of a maximum tensile stress and corresponding strain; and extrapolating and presenting of tensile force at fracture.

2. Method according to claim 1, further comprising the step of calculating and presenting of strain measures.

3. Method according to claim 2, further comprising the step of controlling of pulling speed of the pulling means, in that the controlling of pulling speed of the pulling means depends on the measured relation between tensile force and strain, and in that the controlling of pulling speed of the pulling means is performed by means for pulling control, connected to the logical unit.

4. Method for material testing with a tensile testing device, comprising a first and a second fastening means for attachment of tensile testing specimen, pulling means for displacement of the fastening means relative to each other, means for strain measurement, means for measurement of tensile force, logical unit and presentation unit, said method comprising the steps of:

attaching a tensile testing specimen by clamping its ends in a first and second fastening means, respectively, whereby the clamping is performed by a force independent of the force of the pulling means;

displacement of the fastening means relative each other by applying a force by means of the pulling means;

measuring of the tensile force applied at the fastening means by the pulling means;

measuring of the strain of the tensile testing specimen, comprising measuring of the displacement of the fastening means relative to each other;

collecting measurement results from the means for strain measurements and the means for measuring the tensile force by the logical unit;

presenting measurement results at the presentation unit;

contact-free measuring of the diameter of the tensile testing specimen, whereby the contact-free measuring of the tensile testing specimen is performed simultaneously as the displacement of the fastening means;

presenting of the results of the contact-free measurement of the diameter of the tensile testing specimen together with the result of other results from the tensile testing at the presentation unit;

controlling of pulling speed of the pulling means, in that the controlling of pulling speed of the pulling means depends on the measured relation between tensile force and strain, and in that the controlling of pulling speed of the pulling means is performed by means for pulling control, connected to the logical unit; and reducing the pulling speed to a minimum possible speed when the tensile force has decreased under a predetermined portion of the maximum tensile stress, for minimizing the errors on extrapolating of the tensile force at fracture.

5. Method according to claim 4, further comprising the step of extrapolating and presenting of tensile force at fracture.

6. Method according to claim 4, further comprising the step of calculating and presenting of fracture area at fracture, based on the measurement of the tensile force at fracture.

7. Method according to claim 5, further comprising the step of calculating and presenting a fracture area at fracture, based on the measurement of the tensile force at fracture.

8. Method for material testing with a tensile testing device, comprising a first and a second fastening means for attachment of tensile testing specimen, pulling means for displacement of the fastening means relative to each other, means for strain measurement, means for measurement of tensile force, logical unit and presentation unit, said method comprising the steps of:

attaching a tensile testing specimen by clamping its ends in a first and second fastening means, respectively, whereby the clamping is performed by a force independent of the force of the pulling means;

displacement of the fastening means relative each other by applying a force by means of the pulling means;

measuring of the tensile force applied at the fastening means by the pulling means;

measuring of the strain of the tensile testing specimen, comprising measuring of the displacement of the fastening means relative to each other;

collecting measurement results from the means for strain measurements and the means for measuring the tensile force by the logical unit;

presenting measurement results at the presentation unit;

contact-free measuring of the diameter of the tensile testing specimen, whereby the contact-free measuring of the tensile testing specimen is performed simultaneously as the displacement of the fastening means;

presenting of the results of the contact-free measurement of the diameter of the tensile testing specimen together with the result of other results from the tensile testing at the presentation unit;

determining of a maximum tensile stress and corresponding strain; and reducing the pulling speed to a minimum possible speed when the tensile force has decreased under a predetermined portion of the maximum tensile stress, for minimizing the errors on extrapolating of the tensile force at fracture.

9. Method according to claim 8, further comprising the step of calculating and presenting of strain measures.

10. Method according to claim 8, further comprising the step of calculating and presenting of fracture area at fracture, based on the measurement of the tensile force at fracture.

11. Method according to claim 9, further comprising the step of calculating and presenting of fracture area at fracture, based on the measurement of the tensile force at fracture.

* * * * *